United States Patent
Bidan et al.

(10) Patent No.: US 11,471,399 B2
(45) Date of Patent: Oct. 18, 2022

(54) COMPOSITION FOR SCAR REMODELING

(71) Applicant: PIERRE FABRE DERMO-COSMETIQUE, Boulogne (FR)

(72) Inventors: Catherine Bidan, Labarthe sur Leze (FR); Sandy Rattier, Toulouse (FR)

(73) Assignee: PIERRE FABRE DERMO-COSMETIQUE

(*) Notice: Subject to any disclaimer, the term of this patent is extended or adjusted under 35 U.S.C. 154(b) by 85 days.

(21) Appl. No.: 16/615,335

(22) PCT Filed: May 23, 2018

(86) PCT No.: PCT/EP2018/063472
§ 371 (c)(1),
(2) Date: Nov. 20, 2019

(87) PCT Pub. No.: WO2018/215522
PCT Pub. Date: Nov. 29, 2018

(65) Prior Publication Data
US 2020/0170938 A1    Jun. 4, 2020

(30) Foreign Application Priority Data
May 24, 2017   (FR) .................................. 1754598

(51) Int. Cl.
| | |
|---|---|
| A61K 9/00 | (2006.01) |
| A61P 17/02 | (2006.01) |
| A61K 9/107 | (2006.01) |
| A61K 31/195 | (2006.01) |
| A61K 31/728 | (2006.01) |
| A61K 36/899 | (2006.01) |
| A61K 47/10 | (2017.01) |

(Continued)

(52) U.S. Cl.
CPC .......... *A61K 9/0014* (2013.01); *A61K 9/1075* (2013.01); *A61K 31/195* (2013.01); *A61K 31/728* (2013.01); *A61K 36/899* (2013.01); *A61K 47/10* (2013.01); *A61K 47/14* (2013.01); *A61K 47/26* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 9,849,154 B2 | 12/2017 | Castex-Rizzi et al. | |
| 2002/0077372 A1* | 6/2002 | Gers-Barlag | A61Q 19/00 516/98 |

FOREIGN PATENT DOCUMENTS

| | | | | |
|---|---|---|---|---|
| WO | 2014167039 | 10/2014 | | |
| WO | WO-2014167039 A1 * | 10/2014 | ............. | A61L 15/32 |

OTHER PUBLICATIONS

Scar Treatment (American Society for Surgery of the Hand; www.assh.org/s/, 2016). (Year: 2016).*

(Continued)

*Primary Examiner* — Melissa S Mercier
(74) *Attorney, Agent, or Firm* — Perman & Green, LLP

(57) ABSTRACT

A composition intended for the remodelling treatment of a scar, by means of topical application, in particular, as a massage adjuvant. The composition takes the form of a microemulsion, preferably with a gel texture, containing a lipophilic compound, a wound healing agent, a humectant and an emulsifying agent, as well as a small amount of water.

20 Claims, 1 Drawing Sheet a/ b/

(51) Int. Cl.
*A61K 47/14* (2017.01)
*A61K 47/26* (2006.01)

(56) References Cited

OTHER PUBLICATIONS

Kaur et al. (Role of novel delivery systems in developing topical antioxidants as therapeutics to combat photo aging, Ageing Research Reviews 6 (2007) 271-288). (Year: 2007).*
Otto et al. (Formulation effects of topical emulsions on transdermal and dermal delivery; International Journal of Cosmetic Science, 2009, 31, 1-19) (Year: 2009).*
Kreilgaard (Influence of microemulsions on cutaneous drug delivery, Advanced Drug Delivery Reviews 54 Suppl 1 (2002)S77-S98). (Year: 2002).*
International Search Report, International Application No. PCT/EP2018/063472, dated Jul. 6, 2018.
Database GNPD (Online), Mintel, Feb. 1, 2017, "Ultra Repairing Cream", XP002775619, Database accession No. 4609609, http://www.gnpd.com.
Database GNPD (Online), Mintel, Oct. 1, 2015, "Epitheliale A.H Anti-Marks Ultra-Repairing Cream Duo", XP002775620, Database accession No. 3490843, http://www.gnpd.com.

* cited by examiner

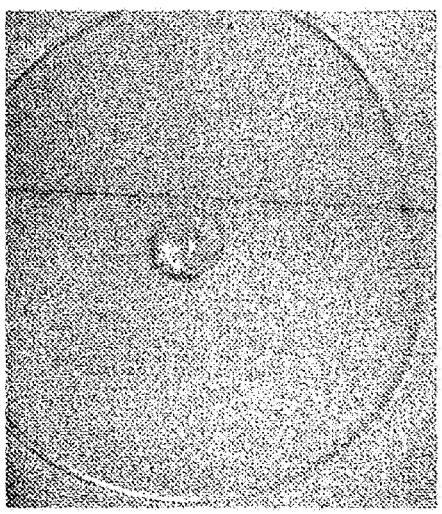
a/
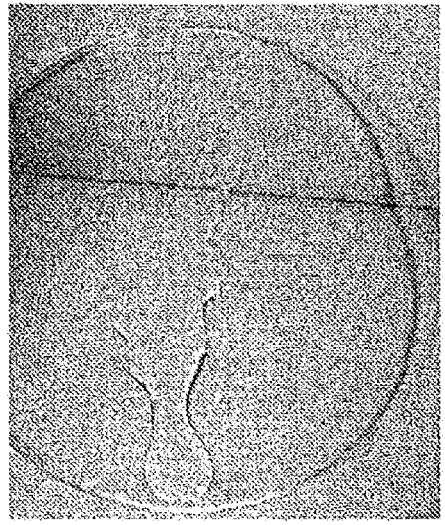
b/

COMPOSITION FOR SCAR REMODELING

CROSS-REFERENCE TO RELATED APPLICATIONS

This Application is a National Stage of International Application No. PCT/EP2018/063472, having an International Filing Date of 23 May 2018, which designated the United States of America, and which International Application was published under PCT Article 21(2) as WO Publication No. 2018/215522 A1, which claims priority from and the benefit of French Patent Application No. 1754598, filed on 24 May 2017, the disclosures of which are incorporated herein by reference in their entireties.

BACKGROUND

1. Field

The presently disclosed embodiment lies in the field of scar remodelling, after reclosure of the lesion which is the source of said scar.

More particularly, the presently disclosed embodiment relates to a composition for the topical treatment of scars, and also to the use of such a composition for remodelling a scar, in particular as massage adjuvant.

2. Brief Description of Related Developments

Wound healing is a physical tissue repair process, which takes place after a wound or lesion, that is to say a destruction of the cutaneous coating, has formed subsequent to the action of an external mechanical agent or to an attack such as a direct trauma, a burn, an injury, a surgical procedure, etc. Wound healing makes it possible to re-establish the skin in its entirety. However, this process generally results in the formation of a visible scar, which forms a mark on the skin.

Processes which assist wound healing are generally used during three successive phases. In a first phase of evolution of the skin lesion, termed vascular or inflammatory phase, the objective of treatments is to stop the bleeding and to clean the wound. This phase occurs within the first hours after lesion formation. It generally lasts a few hours to a few days. In a second phase, termed tissue repair or proliferative phase, treatments aim to facilitate reclosure of the wound and filling of the missing substance, by tissue regeneration. This second phase typically lasts a few days to a few weeks, more specifically two or three days to two or three weeks, depending on the size of the initial lesion. At the end of this phase, the re-epidermization of the initial lesion is complete, and a scar generally remains visible on the skin. Finally, in a third phase, termed maturation or remodelling phase, the objective of treatments is to remodel the scar which has formed during the second phase, and to give it the most aesthetic appearance possible. This phase can last two months to two years. It is during this period that the evolution of the scar actually takes place. Collagen fibres reorganize and densify.

The presently disclosed embodiment lies more particularly within the context of processes for assisting wound healing carried out during the third phase of wound healing, that is to say during the scar remodelling phase, after the initial lesion has completely reclosed, when the re-epidermization of the initial lesion is complete.

During this remodelling phase, the fibres which form can attach to the muscles or to the tissues under the skin, and thus create what is commonly known as adhesions. The latter can be sources of problems and can in particular cause pain and/or stiffness.

In order to overcome this problem, and to promote more generally the positive progression of the scar remodelling phase, and in particular to prevent evolution to an unattractive hypertrophic scar, it is recommended to perform massages, in particular according to the "palpating-rolling" technique, of the scars after complete re-epidermization of the lesion which is responsible for said scars, this being for a period of approximately two months to approximately two years. This mechanical action exerted on the scars makes it possible to soften them, to improve the elasticity of the skin at this site and to free the tissues again, by breaking the adhesions and by re-establishing the slip planes as close to the physiological situation as possible. Massages also improve the tissue vascularization and they decrease pruritus. Massage oils, silicone-based gels or moisturizing ointments can be used during such massages. While these products facilitate the sliding of the masseur's fingers over the skin surface, they however have virtually no efficacy in themselves on the appearance of the scar. Silicone-based gels in addition have an undesirable occlusive effect; moreover, they can be allergenic.

SUMMARY

The presently disclosed embodiment aims to provide a cosmetic and/or dermatological composition which, when used during the scar-remodelling phase, that is to say after complete re-epidermization of the initial lesion, when the lesion is completely reclosed, makes it possible, by topical application, in particular as a supplement to existing massage techniques, to promote scar remodelling and to effectively improve the aesthetic appearance of said scar, thereby decreasing the risk that the individual concerned will definitively retain a scar mark.

An additional objective of the disclosed embodiment is for this composition to contain substantially only ingredients which are natural and/or of natural origin, derived from renewable resources, as opposed to fossil resources, these ingredients being preferably obtainable by means of environmentally friendly processes.

For this purpose, it is provided, according to the presently disclosed embodiment, a cosmetic and/or dermatological composition intended for the topical treatment, more particularly by cell remodelling, of scars. The composition according to the disclosed embodiment is in particular intended to be used as a massage adjuvant.

This composition, which can be applied topically, that is to say, which is in a form suitable for topical application, is in the form of a microemulsion comprising a lipophilic phase and an aqueous phase. It contains:
  a lipophilic compound,
  a wound-healing agent,
  a humectant,
  an emulsifier, capable of forming a microemulsion,
  and water in a total amount of between 1% and 10% by weight relative to the total weight of the composition.

The total amount of lipophilic compound(s) in the composition is preferably greater than or equal to 40% by weight relative to the total weight of the composition. Such a characteristic, combined with the particular form of microemulsion and to the low water content of the composition, advantageously confers on the composition according to the disclosed embodiment organoleptic characteristics very close to those of oils, while at the same time being more viscous than an oil, thereby promoting the use thereof for prolonged massages of the skin surface.

According to the presently disclosed embodiment the term "scars" includes actual scars, that is to say areas of fibrous tissues replacing normal tissues in the dermis after a skin lesion, but also stretch marks, which are defined as thin lines on the skin, with a scar-like appearance, due to the distension or rupture of elastic fibres of the dermis, and more generally any areas of skin that have been weakened after re-epidermization, which present a risk of scar marks. In any event, for the purposes of the presently disclosed embodiment, the term "scar" excludes any wound or lesion not yet completely reclosed.

In the present description, the term "microemulsion" is intended to mean, conventionally in itself, a composition comprising a lipophilic phase, termed fatty phase, and an aqueous phase, one of these phases being dispersed as fine droplets in the other of these phases, in which the size of the droplets of a phase dispersed in the other phase is typically about a few tens of nanometers. Microemulsions are characterized in particular by a thermodynamically stable state, and a translucent appearance. It is within the competence of those skilled in the art to choose the emulsifier suitable for forming a microemulsion in accordance with the disclosed embodiment.

In the present description, the term "wound-healing agent" is intended to mean an agent which promotes repair of the epidermis.

The composition according to the disclosed embodiment is preferentially, in the initial state, in the form of a gel. It can then be described as an oily gel, or a gelled oil, owing to the low proportion of water that it contains, in particular with regard to a high content of lipophilic compound(s) which is preferably greater than or equal to 40% by weight relative to the total weight of the composition. The composition according to the disclosed embodiment thus preferably has, in the initial state, a dynamic viscosity, measured at 22° C., of greater than or equal to 8000 mPa·s. Such a viscosity, and such a gel texture, can be obtained through an appropriate choice of the emulsifier, from emulsifiers having also gelling properties, or else by adding an agent with gelling properties to the emulsifier.

The composition according to the disclosed embodiment preferably has a dynamic viscosity in the initial state, measured at 22° C., of between 10 000 and 22 000 mPa·s, in particular of between 10 000 and 16 000 mPa·s or of between 16 000 and 22 000 mPa·s, depending on the emulsifier, and, possibly, on the gelling agent, used. Such a viscosity is particularly suitable for application to the skin by massage, in particular since the composition does not then flow after it is applied to the skin surface.

The composition according to the disclosed embodiment can consist of a microemulsion of the water-in-oil type, that is to say in which the aqueous phase is dispersed in the form of fine droplets in the lipophilic phase. Preferentially, it is in the form of a microemulsion of oil-in-water type, that is to say in which the lipophilic phase is dispersed in the form of fine droplets in the aqueous phase. Such an aspect of the disclosed embodiment facilitates rinsing of the composition after it has been applied to the skin, which proves for example to be particularly advantageous when the area of skin treated is close to the hair. Here again, it is within the competence of those skilled in the art to choose the emulsifier suitable for obtaining the desired type of microemulsion.

The composition also preferably contains an agent, termed heating agent, capable of producing heat when it is applied to the skin surface, in particular by massage.

The composition according to the disclosed embodiment advantageously combines the effects of a wound-healing agent, which helps to smooth and flatten the scar and reduces redness, tensions and itching; of a humectant which, through an epidermis moisturization effect and itching relief effect, advantageously increases the efficacy of the composition for scar remodelling; and of a lipophilic compound, to the effect of which is preferentially added that of the gel texture of the composition, these effects both facilitating, during massage, the sliding of the fingers over the skin.

The additional presence of a heating agent, which beneficially activates the blood microcirculation owing to the heat released during the application by massage of the composition to the skin surface, further increases the efficacy of the composition for scar remodelling.

The composition according to the disclosed embodiment, by virtue of its microemulsion form and of its low water content, advantageously has a transparent appearance, and organoleptic characteristics very close to those of oils, while at the same time being more viscous than an oil. As a result, it is particularly suitable for massaging the skin, in particular for the prolonged massages recommended for scar remodelling; it does not flow after it has been applied to the skin surface, it has an oily feel which promotes massage, and it penetrates slowly into the skin, for example much more slowly than the ointments proposed by document WO 2014/167039.

The composition according to the disclosed embodiment is also preferably of shear-thinning type, that is to say that its viscosity decreases if the shear stress or the deformation rate which is applied thereto increases. Thus, under the effect of the movements exerted on it during its topical application to the scar, its viscosity decreases, it fluidifies and then immediately penetrates into the epidermis. Such a characteristic, which can be referred to as evolutive texture, proves to be particularly advantageous in the context of an application to scar remodelling. Indeed, it promotes long application times, the user being naturally encouraged to prolong the movements required for the application of the composition, by massaging the scar, so as to totally convert the gel and to allow absorption thereof into the epidermis. As has been set out above, the massaging of a scar, which is thus promoted by the rheological properties of the composition according to the disclosed embodiment, proves to be particularly desirable during the phase of remodelling a scar. It is within the competence of those skilled in the art to determine which ingredients to use in the composition according to the disclosed embodiment in order to obtain such an evolutive texture, in particular through an appropriate choice of the emulsifier.

When topically applied to a scar, by virtue of the combined effects of its constituents, the composition according to the disclosed embodiment proves to be particularly efficient for promoting epidermal remodelling as a supplement to a massage, and improving the aesthetic appearance of scars, by reducing the scar marks. Its efficiency is also measured in terms of immediate and long-lasting soothing of the area of skin concerned, in particular of the sensations of tautness, and also of reduction of pain and of the sensation of stiffness at the level of the scar. By virtue of its heating effect during massage, which activates the blood microcirculation, it also decreases the painful sensation caused by the massage.

The ingredients of the composition according to the disclosed embodiment, are moreover preferentially chosen such that this composition is translucent and has a pleasant appearance.

The wound-healing agent of the composition according to the disclosed embodiment preferably contains hyaluronic acid or a salt thereof.

Hyaluronic acid in particular promotes cell activation and migration, and decreases the consequences of inflammation, which usefully contributes to the skin remodelling. During the scar remodelling phase, which conditions the future aesthetic appearance of the scar, the hyaluronic acid has a structuring effect, in particular by virtue of its action on cell cohesion and neovascularization. It also prevents scab formation.

The wound-healing agent of the composition according to the disclosed embodiment preferentially contains a combination comprising hyaluronic acid or a salt thereof, L-alanyl-L-glutamine and an oat extract. Such a combination particularly significantly increases keratinocyte migration at the scar, through a synergy of the effects of each of its components, the oat extract having in particular a moisturizing effect, and the L-alanyl-L-glutamine dipeptide a glucose-converting effect.

This combination can have one or more, preferably all, of the following characteristics:
the hyaluronic acid is in the form of sodium hyaluronate fragments;
the molecular weight of these sodium hyaluronate fragments is between 50 and 750 kDa;
the oat extract is obtained from oat seedlings;
the hyaluronic acid/oat seedlings extract/L-alanyl-L-glutamine weight ratio is between 2/1/3 and 2/1/5, and for example about 2/1/4.

Such a combination and the characteristics thereof are for example described in document WO 2014/167039.

The composition according to the disclosed embodiment can contain a single wound-healing agent, or a mixture of such agents.

Wound-healing agents that can be present in the composition according to the disclosed embodiment are, for example, sucralfate, madecassoside, panthenol, allantoin, aloe vera or honey.

The total amount of wound-healing agent(s) in the composition according to the disclosed embodiment is preferably between 0.01% and 3% by weight relative to the total weight of the composition.

The composition according to the disclosed embodiment can also contain a single humectant, or a mixture of such humectants.

A humectant contained in the composition according to the disclosed embodiment can in particular be a polyol. It can in particular consist of a polyethylene glycol, of a polypropylene glycol, such as dipropylene glycol, etc.

Preferentially, the composition according to the disclosed embodiment contains glycerol, which offers the advantage of constituting by itself a physiological humectant, emollient and moisturizing agent, and a heating agent in the meaning of the present disclosed embodiment, that is to say an agent which gives off heat during massage.

The glycerol also makes it possible to adjust the transparency of the composition.

It in particular has a high capacity for retaining water at the skin surface, and therefore a high capacity for maintaining surface moisturization.

Glycerol also advantageously makes it possible to use water-soluble wound-healing agents in the composition according to the disclosed embodiment, without requiring the incorporation of large amounts of water in the composition. This proves to be particularly useful when the wound-healing agent is a combination of hyaluronic acid or a salt thereof, of L-alanyl-L-glutamine and of an oat extract, as described above. Such a combination, which is not soluble in fatty substances, can be solubilized in glycerol without necessitating large amounts of water. It is thus possible to prepare a composition in the form of a viscous oily gel, which is particularly suitable for massages, containing a water-soluble wound-healing active agent.

Glycerol also offers the advantage of being biobased, and readily available in natural form or a form of natural origin. It can for example be extracted from coconut oil or from palm oil.

The total amount of humectant(s), and more particularly of glycerol, in the composition can in particular be between 10% and 50% by weight relative to the total weight of the composition, preferably greater than 25% and less than or equal to 50% by weight relative to the total weight of the composition. It can for example be equal to approximately 30% by weight, relative to the total weight of the composition.

A glycerol content of greater than 25% w/w provides in particular a considerable release of heat during massage, and provides the skin with considerable moisturization.

The composition according to the disclosed embodiment can contain a single lipophilic compound, or a plurality of such compounds.

The total amount of lipophilic compound(s) in the composition is preferably greater than or equal to 40% by weight relative to the total weight of the composition, and preferentially between 40% and 70% by weight relative to the total weight of the composition.

The lipophilic compound can in particular be chosen from triglycerides, preferably medium-chain triglycerides, that is to say triglycerides in which the hydrocarbon-based chain comprises from 8 to 12 carbon atoms, and preferentially triglycerides of capric and/or caprylic acid, or any one of the mixtures thereof.

The capric and/or caprylic acid triglycerides, also called caprylic/capric triglycerides, advantageously have an emollient effect, which further increases the degree of moisturization of the skin, and a nutritive effect. They also come from renewable resources.

The composition according to the disclosed embodiment can contain a single emulsifier, or a plurality of such emulsifiers.

This or these emulsifier(s) is (are) preferably chosen such that the composition is in the form of a stable translucent microemulsion having the texture of a gel, preferably with shear-thinning properties, the composition comprising a fatty phase and an aqueous phase, formed for example, respectively, of at least one lipophilic compound such as caprylic/capric triglycerides, and of at least one polyol such as glycerol and a small amount of water.

The emulsifier preferably has gelling properties.

The emulsifier preferably contains at least, or consists of at least, one compound chosen from:
sugar esters, preferably chosen from disaccharide esters such as sucrose esters, lactose esters, maltose esters, and monosaccharide esters such as glucose esters, fructose esters, galactose esters; the sucrose esters being particularly preferred; such an ester or a mixture of such esters being preferentially present in the composition according to the disclosed embodiment in a total amount of between 1% and 10%, preferably between 1% and 5%, by weight relative to the total weight of the composition;

esters of fatty acids and of polyglycerol; such an ester or a mixture of such esters being preferentially present in the composition according to the disclosed embodiment in a total amount of between 1% and 15% by weight relative to the total weight of the composition;

or any one of the mixtures thereof.

The emulsifier can in particular contain, as a mixture, a surfactant, a co-surfactant and a lipophilic compound or fatty substance.

It can for example contain, as a mixture:

a sugar ester, preferably a disaccharide ester, such as a sucrose, lactose or maltose ester, or any one of the mixtures thereof; and preferentially a sucrose ester; or else a monosaccharide ester, such as a glucose, fructose or galactose ester; or a mixture of such esters;

a polyol, in particular glycerol;

and a lipophilic compound chosen from triglycerides, preferably medium-chain triglycerides, and preferentially capric and/or caprylic acid triglycerides, or any one of the mixtures thereof.

The sucrose ester can in particular be sucrose laurate, or any other sucrose ester comprising a hydrocarbon-based chain, in particular an alkyl chain, having from 4 to 30 carbon atoms, preferably from 12 to 18 carbon atoms, it being possible for this chain to be linear or branched, saturated or unsaturated, and even cyclic or aromatic.

The sucrose ester is preferentially present in the composition according to the disclosed embodiment in a total amount of between 1% and 10%, preferably between 1% and 5%, by weight relative to the total weight of the composition.

The use of glycerol and of caprylic/capric triglycerides in the emulsifier according to the disclosed embodiment is particularly advantageous in the particular aspects of the disclosed embodiment of the composition described above, in which the lipophilic compound is a caprylic/capric triglyceride and/or the humectant is glycerol. The total number of components in the composition according to the disclosed embodiment is then reduced.

In particular aspects of the disclosed embodiment of the composition, the emulsifier contains, as a mixture:

6.5% by weight, relative to the total weight of the emulsifier, of sucrose laurate, 46% by weight, relative to the total weight of the emulsifier, of glycerol, 35% by weight, relative to the total weight of the emulsifier, of caprylic/capric acid triglycerides, 13.5% by weight, relative to the total weight of the emulsifier, of water.

Such an emulsifier, which advantageously has considerable gelling properties, and which makes it possible to form a microemulsion of the oil-in-water type in the form of a gel with shear-thinning properties, is sold under the name Sucragel® CF by the company Alfa.

It proves to be particularly advantageous in the context of the presently disclosed embodiment.

In other particular aspects of the disclosed embodiment, the emulsifier is chosen from esters of fatty acids and of polyglycerol. The emulsifier is, for example, polyglyceryl-10 myristate, as sold for example under the name SFACE M-1001 by the company Rossow Cosmétiques. Such an emulsifier also makes it possible to form a microemulsion of the oil-in-water type in the form of a gel with shear-thinning properties. It is preferably present in the composition according to the disclosed embodiment in a total amount of between 1% and 15% by weight, relative to the total weight of the composition.

The total amount of emulsifier(s) in the composition is preferably between 1% and 30% by weight relative to the total weight of the composition, in particular, depending on the emulsifier(s) used, for example for Sucragel® CF, between 6% and 30% by weight relative to the total weight of the composition.

Preferentially, the total amount of water in the composition is between 1% and 8% by weight, relative to the total weight of the composition.

The composition according to the disclosed embodiment can contain other active agents, in particular via the topical route, for example chosen from antioxidants, such as vitamin E, ultraviolet-ray blockers, vitamins, oils such as olive oil, essential oils, etc., or a mixture of such compounds.

It can also contain any additive that is conventional in itself for a cosmetic and/or dermatological composition, for example one or more of the ingredients hereinafter: dye, neutralizing agent, etc.

Preferentially, it is free of preservative. It is also preferentially devoid of fragrance, of disinfecting agent, or else of antimicrobial, bactericidal or bacteriostatic, fungistatic or fungicidal agent, so that it is friendly to the skin equilibrium.

It is preferentially free of silicone. In particular it does not have any occlusive effect on the skin.

The composition according to the disclosed embodiment is also preferentially devoid of butters or waxes in its lipophilic phase.

The composition according to the disclosed embodiment preferably contains a low total number of ingredients, in particular a total number of ingredients of less than 12, and preferably less than 10.

Advantageously, none of these ingredients is of the type with a risk of intolerance, or of the type which modifies the biology of the skin. All of them are preferably physiologically compatible ingredients.

Preferentially, the vast majority of the ingredients making up the composition according to the disclosed embodiment are natural or of natural origin, and can be obtained by ecological/environmentally friendly processes.

The composition according to the disclosed embodiment can be packaged in any receptacle that is conventional in itself. It can in particular be packaged in a tube.

The composition according to the disclosed embodiment can be used for the treatment of a scar formed on the skin of a mammal, in particular of a human being, by topical application of this composition to the scar.

According to another aspect, the presently disclosed embodiment thus relates to the use of a composition according to the disclosed embodiment, having in particular one or more of the characteristics above, for the treatment, in particular the remodelling, of a scar formed on the skin of a mammal, in particular of a human being, by topical application of said composition to said scar, and possibly the surrounding skin area.

This treatment aims in particular to improve the aesthetic appearance of the scar, and also the comfort of the individual bearing the scar, by relieving the itching and pain associated with this scar.

According to the disclosed embodiment, the use of the composition comprises the following steps:

the topical application of the composition to the surface of the scar, in an effective amount for treating said scar, the massaging of the scar, preferably by means of a "palpating-rolling" method, so as to cause the composition to penetrate into the epidermis.

The massaging carried out in particular causes the composition to change from a gel form to a more fluid form, which immediately penetrates into the epidermis.

Preferentially, the composition is applied to the surface of the scar by circular movements, which cause heating of the skin, preparing the latter for the massaging by activation of the blood microcirculation in this area. Advantageously added to this is the heating effect of the heating agent preferentially present in the composition.

The actual massaging, carried out in a second step, in particular by means of the "palpating-rolling" method, for its part exerts a softening effect on the skin at the level of the scar, it acts on the collagen fibres and contributes considerably to optimal remodelling of the scar.

These steps are preferably carried out once or twice a day.

The composition according to the disclosed embodiment is preferably used for a period of two months to two years starting from the complete re-epidermization of the lesion responsible for the scar.

The composition can be applied both to the skin of the face and to that of the body or of the scalp. The individual treated can equally be an infant, a child or an adult.

At the end of application, the composition according to the disclosed embodiment leaves on the skin surface a protective film, giving the effect of a breathing, moisturizing, non-fatty and non-tacky second skin, which gives comfort back to the treated individual and reduces the desire to scratch.

The disclosed embodiment is also expressed in terms of a process for treating, in particular remodelling, a scar formed on the skin of a mammal, in particular of a human being, by topical application to said scar, and possibly the surrounding skin area, of an effective amount of a composition according to the disclosed embodiment, having in particular one or more of the characteristics above.

This process can correspond to one or more of the characteristics described above with reference to the use of the composition according to the disclosed embodiment.

This process can in particular be a process for cosmetic treatment of the scar, aimed at improving the aesthetic appearance thereof.

BRIEF DESCRIPTION OF THE DRAWINGS

The characteristics and advantages of the disclosed embodiment will emerge more clearly in the light of the examples of implementation below, which are provided simply by way of illustration and which are in no way limiting of the disclosed embodiment, with the support of FIG. 1, which illustrates the flow capacity a/ of a composition according to the disclosed embodiment, and b/ of a prior art oil composition, 1 g of each of the compositions having been deposited respectively on a watch glass, the latter being inclined so as to cause the composition to flow at its surface.

DETAILED DESCRIPTION

Example 1

A composition in accordance with the presently disclosed embodiment is prepared from the ingredients indicated in Table 1 below. For each of these ingredients, the amount is indicated as percentage by weight, relative to the total weight of the composition, it being understood that the amount of water in the composition is at least 1%, and does not exceed 10%, by weight relative to the total weight of the composition.

TABLE 1

Composition according to the disclosed embodiment

| Ingredient | Amount (% w/w) |
| --- | --- |
| Sucragel ® CF | 10-30 |
| Caprylic/capric triglycerides | 40-60 |
| Olive oil | 1-6 |
| Glycerol | 10-40 |
| Sodium hyaluronate | 0.01-1 |
| Oat seedling extract | 0.01-1 |
| L-Alanyl-L-glutamine | 0.01-1 |
| Vitamin E | 0.1-1.5 |
| Water | qs |

The dynamic viscosity of this composition in the initial state is measured by means of a Lamy Rheology RM180 Rheomat rheometer (measuring spindle: size 3; rotational speed: 7.61 s$^{-1}$; temperature: 22° C.).

This dynamic viscosity is between 16 000 and 22 000 mPa·s.

In order to evaluate the flow capacity of this composition, 1 g of composition is deposited on a watch glass, and the watch glass is inclined so as to cause the composition to flow on its surface. By way of comparative example, the same experiment is carried out with the oil mixture sold under the name Bi-Oil by the Omega Pharma laboratories. The results obtained are shown in FIG. 1. As can be seen, while the Bi-Oil composition flows along the surface of the glass (in b/ in the FIGURE), the composition according to the disclosed embodiment does not flow at all (in a/ in the FIGURE), for the same inclination of the glass.

This composition according to the disclosed embodiment, which in the initial state is in the form of an oily gel, is applied to the scar after total closure of the lesion which is responsible for said scar, preferably at a rate of once or twice a day. To this effect, circular movements are first of all carried out for a few minutes, followed by palpating-rolling massage.

During the first phase, the gel form prepares the skin for the massage by activating the microcirculation.

During the second phase, the palpating-rolling massage softens the skin, acts on the collagen and elastin fibres and thus contributes to optimal remodelling of the skin.

Such a treatment provides long-lasting soothing of the sensations of tautness, and promotes epidermal remodelling. After a few weeks of treatment, scar marks and stretch marks are less visible.

By way of comparative example, a similar composition is prepared, but in which the Sucragel® CF is replaced as emulsifier with a mixture of cetearyl glucoside and of cetearyl alcohol proposed by document WO 2014/167039 in the example thereof which appears on page 12. This mixture of compounds does not make it possible to form a microemulsion, nor even a stable emulsion, so that the composition obtained does not prove to be in any way suitable for prolonged massaging of the skin surface.

Example 2

A composition in accordance with the presently disclosed embodiment is prepared from the ingredients indicated in Table 2 below. For each of these ingredients, the amount is indicated as percentage by weight, relative to the total weight of the composition, it being understood that the amount of water in the composition is at least 1%, and does not exceed 10%, by weight relative to the total weight of the composition.

TABLE 2

Composition according to the disclosed embodiment

| Ingredient | Amount (% w/w) |
| --- | --- |
| Polyglyceryl-10 Myristate | 1-15 |
| Caprylic/capric triglycerides | 40-70 |
| Olive oil | 1-6 |
| Glycerol | 10-50 |
| Sodium hyaluronate | 0.01-1 |
| Oat seedling extract | 0.01-1 |
| L-Alanyl-L-glutamine | 0.01-1 |
| Vitamin E | 0.1-1.5 |
| Water | qs |

This composition is in the form of an oily gel. Its viscosity in the initial state, measured as indicated above in Example 1, at 22° C., is between 10 000 and 16 000 mPa·s.

This composition is applied to the scar under the same conditions as those described above with reference to Example 1.

Here again, the treatment provides long-lasting soothing of the sensations of tautness and promotes remodelling of the epidermis. After a few weeks of treatment, scar marks and stretch marks are also less visible.

What is claimed is:

1. A scar treatment composition, applicable topically, comprising a lipophilic phase and an aqueous phase in the form of a microemulsion with one of the phases being dispersed as fine droplets in the other phase, said composition containing:
   one or more lipophilic compounds in a total amount of greater than or equal to 40% by weight relative to the total weight of the composition;
   a wound-healing agent;
   a humectant;
   an emulsifier; and
   water in a total amount between 1% and 10% by weight relative to the total weight of the composition.
2. The composition according to claim 1, having a dynamic viscosity at 22° C. of greater than or equal to 8000 mPa.s.
3. The composition according to claim 1, in the form of a microemulsion of oil-in-water type.
4. The composition according to claim 1, wherein the wound-healing agent contains hyaluronic acid or a salt thereof.
5. The composition according to claim 4, wherein the wound-healing agent contains a combination comprising hyaluronic acid or a salt thereof, L-alanyl-L-glutamine and an oat extract.
6. The composition according to claim 1, wherein the total amount of wound-healing agent(s) in the composition is between 0.01% and 3% by weight relative to the total weight of the composition.
7. The composition according to claim 1, containing glycerol as a heating agent, which produces heat when it is applied to the skin surface.
8. The composition according to claim 1, wherein said humectant is a polyol.
9. The composition according to claim 8, wherein said humectant is glycerol.
10. The composition according to claim 9, wherein the total amount of glycerol is between 10% and 50% by weight relative to the total weight of the composition.
11. The composition according to claim 1, wherein the one or more lipophilic compounds are selected from the group consisting of triglycerides and mixtures of triglycerides.
12. The composition according to claim 1, wherein the emulsifier contains at least one compound selected from the group consisting of:
   sugar esters;
   esters of fatty acids and polyglycerol;
   or any one of the mixtures thereof.
13. The composition according to claim 1, wherein the emulsifier contains, as a mixture:
   a sugar ester;
   a polyol;
   at least one lipophilic compound selected from the group consisting of triglycerides and mixtures of triglycerides.
14. The composition according to claim 1, wherein the total amount of emulsifier(s) in the composition is between 1% and 30% by weight relative to the total weight of the composition.
15. The composition according to claim 1, containing an antioxidant.
16. The composition according to claim 1, which is free of preservative.
17. A method for treating a scar, comprising a step of topically applying a composition according to claim 1, to said scar.
18. The method according to claim 17, comprising, after: topically applying the composition to the surface of the scar, a step of massaging of the scar.
19. The method according to claim 17, implemented for a period of two months to two years starting from complete re-epidermization of a lesion responsible for the scar.
20. The composition according to claim 1, wherein the emulsifier contains, as a mixture:
   a sucrose ester;
   glycerol; and
   capric and/or caprylic acid triglycerides.

* * * * *